(12) United States Patent
Mei et al.

(10) Patent No.: US 11,209,407 B2
(45) Date of Patent: Dec. 28, 2021

(54) SYSTEM FOR DETECTION AND ANALYSIS OF FIBROUS ROOT SYSTEM ARCHITECTURE OF PLANT

(71) Applicant: Shanghai Agrobiological Gene Center, Shanghai (CN)

(72) Inventors: Hanwei Mei, Shanghai (CN); Qiaojun Lou, Shanghai (CN); Ming Yan, Shanghai (CN); Fangjun Feng, Shanghai (CN); Huan Gao, Shanghai (CN)

(73) Assignee: Shanghai Agrobiological Gene Center, Shanghai (CN)

( * ) Notice: Subject to any disclaimer, the term of this patent is extended or adjusted under 35 U.S.C. 154(b) by 0 days.

(21) Appl. No.: 17/096,181

(22) Filed: Nov. 12, 2020

(65) Prior Publication Data

US 2021/0293767 A1    Sep. 23, 2021

(30) Foreign Application Priority Data

Mar. 23, 2020 (CN) .......................... 202010210117.8

(51) Int. Cl.
*G01N 21/00* (2006.01)
*G01N 33/00* (2006.01)
*G01N 21/39* (2006.01)
*G01N 21/84* (2006.01)

(52) U.S. Cl.
CPC ......... *G01N 33/0098* (2013.01); *G01N 21/39* (2013.01); *G01N 21/84* (2013.01); *G01N 2021/8444* (2013.01); *G01N 2021/8466* (2013.01)

(58) Field of Classification Search
CPC ............. G01N 21/255; G01N 29/2418; G01N 21/1702; G01N 21/171; G01N 21/1717
USPC ........................................................ 356/432
See application file for complete search history.

(56) References Cited

U.S. PATENT DOCUMENTS

| | | | |
|---|---|---|---|
| 2015/0015697 A1* | 1/2015 | Redden ................. | G01B 11/24 348/89 |
| 2017/0219711 A1* | 8/2017 | Redden ................. | A01G 7/06 |

* cited by examiner

*Primary Examiner* — Md M Rahman
(74) *Attorney, Agent, or Firm* — Saliwanchik, Lloyd & Eisenschenk (57) ABSTRACT

Provided is a system for detection and analysis of a fibrous root system architecture of a plant, including a plant pot having at least one slit area extending through a cross section in an axial direction, at least one laser measuring unit, and a data analyzing unit, where each laser measuring unit has a laser transmitter and a receiver disposed corresponding to the slit area in such a manner that a laser beam emitted from the laser transmitter to the receiver goes across the cross section of the plant pot; measurement on all roots in the slit area is realized by a rotating stage, and the laser measuring unit swinging horizontally around the laser transmitter within a predetermined angle range; and the data analyzing unit is configured to perform statistical analysis on the roots of a plant to be measured according to laser measuring results.

10 Claims, 5 Drawing Sheets

SYSTEM FOR DETECTION AND ANALYSIS OF FIBROUS ROOT SYSTEM ARCHITECTURE OF PLANT

CROSS-REFERENCE TO RELATED APPLICATION

This application claims the benefit under 35 U.S.C. § 119 of Chinese Application No. 202010210117.8, filed Mar. 23, 2020, which is hereby incorporated in its entirety.

TECHNICAL FIELD

The disclosure belongs to the technical field of plant phenotype identification, and particularly relates to a system for detection and analysis of a fibrous root system architecture of a plant by using a non-contact detection technique with high detection accuracy.

BACKGROUND

A plant root system has indispensable functions. It not only fixes and supports various organs of the plant shoot system, such as stem, leaf, flower and fruit, but is also the main organ for the plant to absorb water and mineral nutrients. The plant root system also plays a role in nutrient storage and physiological and biochemical regulation. A root system architecture is not only controlled by the genotype of the plant, but also largely affected by environmental conditions. The root system architecture and the root vitality largely determine yield and stress resistance of a crop.

Deep-rooting, one of the important features of the root system architecture, refers to a higher proportion of roots distributed in a deeper soil layer. The ratio of deep roots to shallow roots is closely related to the growth angles of roots. For example, in rice, those growing at an angle of less than 50 degrees with respect to the horizontal are considered as shallow roots, while those growing at an angle of greater than 50 degrees with respect to the horizontal are considered as deep roots (Kato Y et al. 2006, Plant Soil). Thus, a "basket method" to identify the ratio of deep roots to shallow roots was proposed, where rice plants were grown at the top central position of a porous plastic or stainless steel basket with a ratio of bottom radius to depth of 0.84; the basket was buried in the soil for the plants to grow for a period of time; then, the basket was dig out and the roots stretching out from the bottom of the basket were manually counted as the deep roots; and the roots stretching out from the sides of the basket were counted as the shallow roots (Uga Y et al. 2009, Breed Sci).

Due to growing of a root system in the soil and complicated three-dimensional distribution thereof, it is very technically difficult to investigate the root system architecture, especially difficult to achieve non-destructive, continuous and high-throughput detection.

For a long time, people have tried every means to observe and measure the root system architectures of plants, including detection techniques for roots in actual soil, and observation methods for roots in artificially simulated scenarios in laboratories or greenhouses. For example, the root system in the soil is directly dug out or the cut roots in each soil layer are manually measured. In order to maintain the three-dimensional distribution of the roots after the soil is washed off, a three-dimensional meshed wire cage can be buried in the soil in advance, or a hollow cylinder can be buried in the soil in advance to facilitate soil mass digging (such as Shovelomics corn crown root analysis method). The roots close to the surface can be observed in situ through a glass window or transparent root pipe preinstalled in a large underground root chamber. Alternatively, part of visible roots can be observed in situ by means of an embedded micro-root pipe and a matching scanning probe.

The strategies of cultivating plants and observing the root system architectures in artificial scenarios are mainly classified into: 1) hydroculture methods, which permit convenient observation, but have great differences between the resulting three-dimensional root system architectures and those in soil; 2) image analysis and 3D distribution reconstruction of roots in transparent gel which is only suitable for seedlings and greatly differs from the environment in the soil; 3) methods of observing roots by compressing the roots in a 2D plane or a thin-layer substrate using a plurality of clamping plates, which are convenient for high-throughput continuous observation, but may cause great changes in spatial distribution; 4) methods of soil culture of roots in PVC pipes, where the soil environment in the field can be well simulated and different treatments can be applied conveniently, but the roots can be washed for observation only after the test is completed, resulting in loss of the original three-dimensional distribution information of the roots; and 5) X-ray computed tomography (CT) and magnetic resonance imaging (MRI) techniques, which can permit in vivo three-dimensional detection of plant roots, where high-resolution large-field-of-view instruments used are expensive and affected by compositions and water contents of substrates, while the X-ray CT technique requires high transparency special media.

All in all, the existing root system architecture measuring techniques are either destructive in the implementation process or only capable of observing a small number of roots close to the surface of the window, and thus are not ideal in comprehensive optimization on technical elements such as simulation of the soil environment in the field, non-destructive continuous monitoring, and low-cost high-throughput monitoring.

SUMMARY

The disclosure addresses the above problems, and aims at providing a system for detection and analysis of a fibrous root system architecture of a plant by using a non-contact detection technique with high detection accuracy.

The disclosure provides a system for detection and analysis of a fibrous root system architecture of a plant, including:
a plant pot for growing a plant to be measured, the plant pot having at least one slit area extending through a cross section in an axial direction;
at least one laser measuring unit, each laser measuring unit having a laser transmitter and a receiver arranged correspondingly to the slit area in such a manner that a laser beam emitted from the laser transmitter to the receiver goes across the cross section of the plant pot;
an arc-shaped measuring bow for mounting the laser measuring unit and driving the laser measuring unit to swing horizontally around the laser transmitter within a predetermined angle range to realize measurement on roots in an effective sector;
a rotating stage for driving the plant pot to rotate step by step by an equal angle to obtain measuring results of roots in a plurality of effective sectors sequentially at different angles, thus realizing measurement on all roots in the slit area; and a data analyzing unit connected to the laser measuring unit to statistically analyze the roots of the plant to be measured based on the laser measuring result.

The system for detection and analysis of a fibrous root system architecture of a plant provided by the disclosure may also have such features below: the plant pot includes a bottom pot and at least one insert pot capable of being inserted into the bottom pot;

the slit area is formed between the bottom pot and the adjacent insert pot; and the bottom of the insert pot is of a mesh structure having a mesh aperture greater than a maximum root diameter of the plant to be measured.

The system for detection and analysis of a fibrous root system architecture of a plant provided by the disclosure may also have such features below: at least two insert pots are used with the slit area being formed between every two adjacent insert pots;

the number of the laser measuring units is the same as that of the insert pots; and each slit area is provided with the laser transmitter and the receiver.

The system for detection and analysis of a fibrous root system architecture of a plant provided by the disclosure may also have such features below: the bottom pot and the insert pot or every two adjacent insert pots are connected and fixed by means of three pins and corresponding pin holes.

The system for detection and analysis of a fibrous root system architecture of a plant provided by the disclosure may also have such features below: an end, corresponding to the laser transmitter, of the arc-shaped measuring bow is fixed to a column which is mounted on a fixed base of the rotating stage.

The system for detection and analysis of a fibrous root system architecture of a plant provided by the disclosure may also have such features below: a laser beam emitted by the laser transmitter has a diameter of less than 1 mm, and the laser measuring result is a beam path passing signal or a beam path blocking signal obtained by a laser beam emitted by the laser transmitter to the corresponding receiver.

The system for detection and analysis of a fibrous root system architecture of a plant provided by the disclosure may also have such features below: during the rotation of the arc-shaped measuring bow, the laser measuring unit performs detection for a plurality of times at a predetermined time interval, thereby defining a detection sector.

The system for detection and analysis of a fibrous root system architecture of a plant provided by the disclosure may also have such features below: the plant pot is placed on the rotating stage in such a manner that the centers of the two are vertically coaxial with each other; and during the process that the plant pot rotates a circle step by step by an equal angle, the laser measuring unit swings once at each interval between steps to measure roots, thereby obtaining measuring results of roots for a plurality of detection sectors.

The system for detection and analysis of a fibrous root system architecture of a plant provided by the disclosure may also have such features below: the data analyzing unit reconstructs the coordinate positions of all detection beam paths in the slit area by analysis, and performs fault localization and counting of roots in the cross section according to the coverage of the laser beams in the cross section and the intersection position information of blocked beam paths.

The system for detection and analysis of a fibrous root system architecture of a plant provided by the disclosure may also have such features below: the data analyzing unit also performs integrated analysis on the detection data of the positions and numbers of roots in the cross sections of a plurality of slit areas so as to realize the reconstruction of a pseudo-three-dimensional root system architecture of the plant to be measured.

Purposes and Effects of the Disclosure

According to the system for detection and analysis of a fibrous root system architecture of a plant provided in the disclosure, the plant to be measured is grown in the plant pot, and the plant pot is driven by the rotating stage to coaxially rotate step by step by an equal angle at different time points in the growth period of the plant. The laser measuring unit swings horizontally around the laser transmitter within a predetermined angle range at each interval between steps. While swinging, the laser transmitter emits laser beams to the receiver, and reads transmitted and blocked beam signals at a predetermined time interval. The positions and the number of roots in the cross section corresponding to each slit area are obtained by analysis of the measuring results of all laser beams. The system just uses laser beams to measure roots in the slit areas with no contact with the plant roots and thus no damage to the plant roots. Moreover, the slit area is formed in at least one position of the plant pot, so that the roots throughout the cross section in the desired position can be measured. The measuring results of a plurality of cross sections can be used to construct a pseudo-three-dimensional root system architecture.

DETAILED DESCRIPTION

The disclosure will be further described below by way of example, but not limited to the scope of the examples.

Examples

The technical solution of this example aims to overcome the shortcomings of the phenotype identification of a plant root system architecture in the prior art, establish a plant cultivation method with horizontal detection slit areas preformed in soil mass in a plant pot, and permit fault localization and counting of plant roots in the slit areas using laser beams and further reconstruction of a pseudo-three-dimensional plant root system architecture from the fault localization data of a plurality of slit areas up and down.

Figure 1:
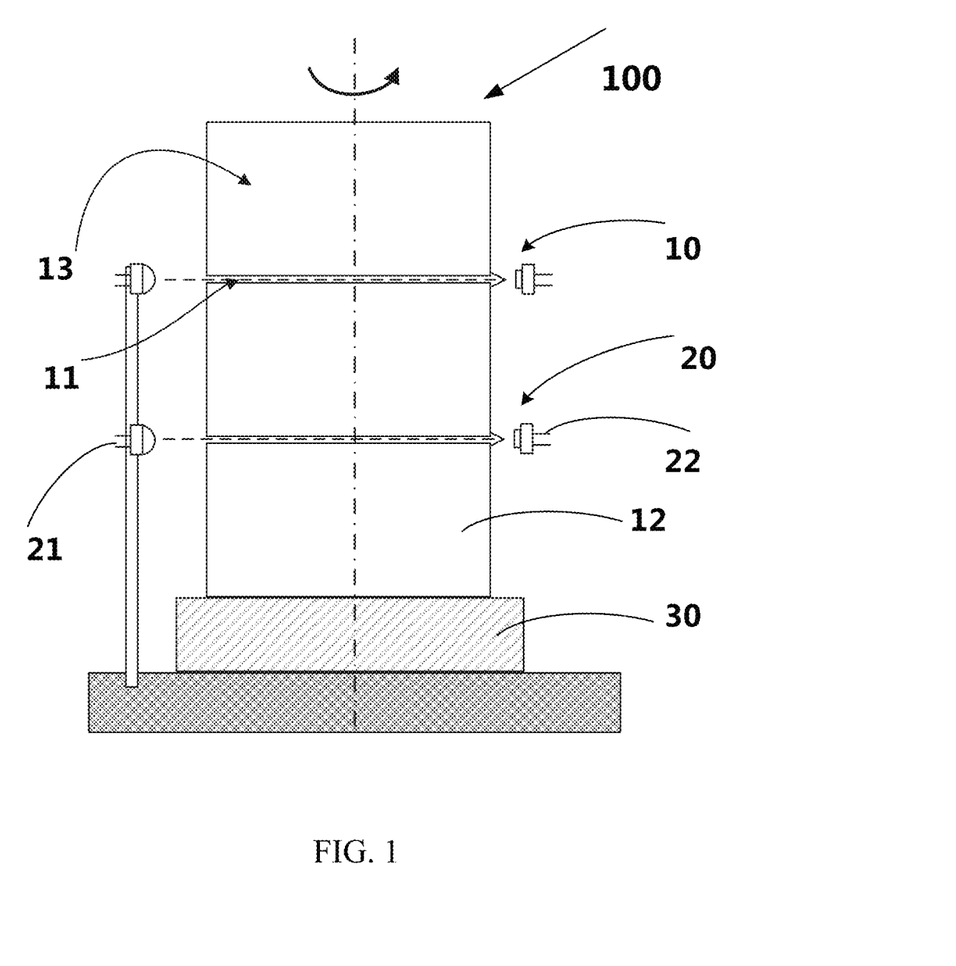
FIG. 1 is a structural schematic diagram of a system for detection and analysis of a fibrous root system architecture of a plant according to an example of the disclosure.

FIG. 1 is a structural schematic diagram of a system for detection and analysis of a fibrous root system architecture of a plant according to an example of the disclosure.

As shown in FIG. 1, there is disclosed herein a system 100 for detection and analysis of a fibrous root system architecture of a plant. The system 100 for detection and analysis, as a technical solution of non-contact detection, includes a plant pot 10, two laser measuring units 20, a rotating stage 30, and a data analyzing unit not shown in the figure.

The plant pot 10 is used to grow a plant to be measured, which is cylindrical on the whole and has two slit areas 11 extending through cross sections in an axial direction. The two slit areas 11 are exactly the same in structure and size and just formed at different positions of the plant pot 10 in the axial direction, that is, the two slit areas 11 correspond to different depth positions of the root system of the plant to be measured.

The plant pot 10 includes a bottom pot 12 and two insert pots 13 that can be inserted in sequence and stacked up and down above the bottom pot 12. The cylindrical plant pot is formed by one bottom pot 12 and two insert pots 13.

In this example, the bottom pot 12 is a plastic closed-ended round pot, and three equal-angled connecting shackles with pin holes are distributed at equal angles on the outer side of the upper edge of the pot wall.

In this example, the two insert pots 13 are exactly the same in structure and function and stacked in sequence up and down. Here, only one of the insert pots 13 is described in detail, while the detailed description of the other is omitted.

Figure 2:
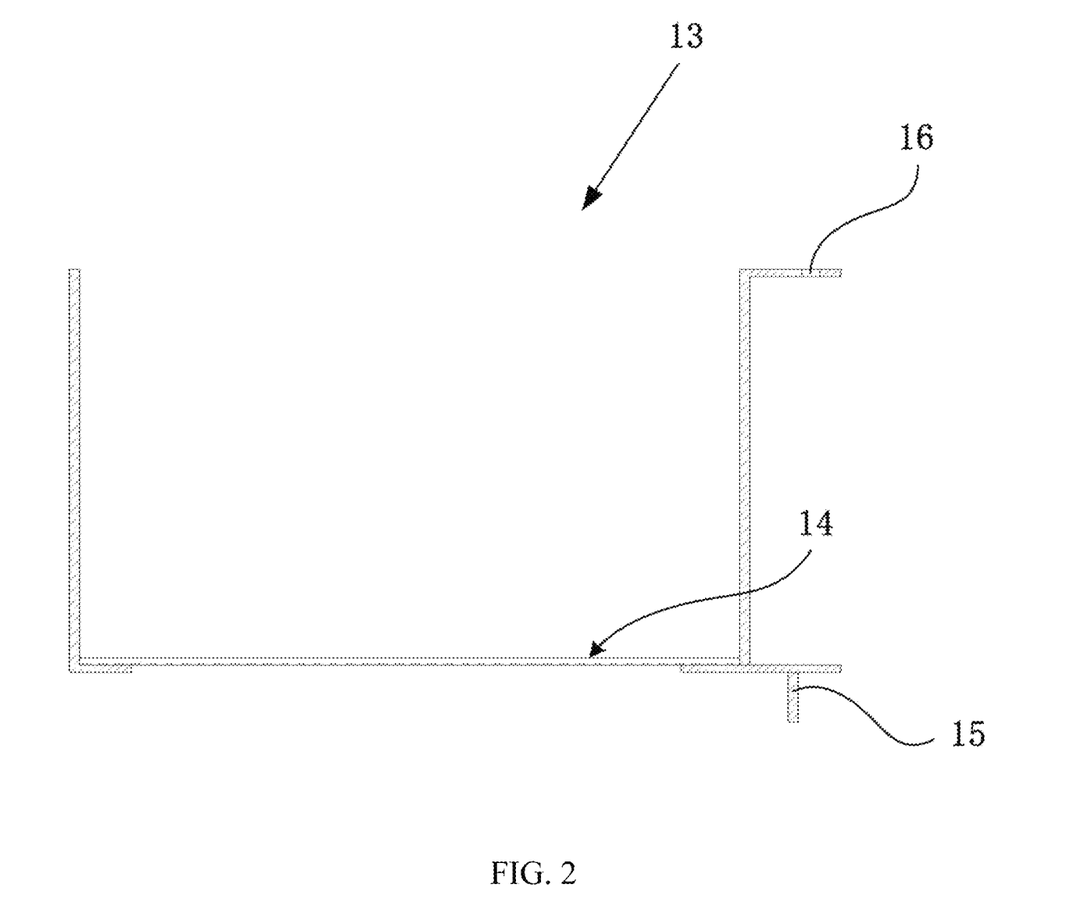
FIG. 2 is a structural schematic diagram of an insert pot according to an example of the disclosure.

FIG. 2 is a structural schematic diagram of an insert pot according to an example of the disclosure.

As shown in FIG. 2, the bottom of the insert pot 13 is of a mesh structure 14 having a mesh aperture greater than a maximum root diameter of the plant to be measured. Specifically, a mesh plate having the minimum aperture of 2 mm can be integrally formed with the bottom of the insert pot 13, or a mesh plate manufactured independently can be placed in a hollow cylinder slightly inwardly buckled. Three connecting shackles with pins 15 are distributed at equal angles on the lower edge of the pot wall of the insert pot 13, while three connecting shackles with pin holes 16 are distributed at the same positions on the upper edge.

The two insert pots 13 stacked up and down are sized to accurately match the positions of the connecting shackles. The bottom pot 12 and the insert pot 13, and the two adjacent insert pots 13 are connected and fixed by inserting the pins into the pin holes. At the joint of each layer, namely, between the lower wall edge of the upper pot and the upper wall edge of the lower pot, uniform gaps of 3 mm to 5 mm are formed, and then a slit area 11 is formed.

In addition, before filling of sandy soil or other substrates in each insert pot 13, a thin layer of material such as sponge or germinating paper can be laid on the bottom of the insert pot 13 to inhibit the sandy soil from leaking out of the holes. Moreover, it is desirable to fill a lower pot with sandy soil or other substrates as much as possible without exceeding the upper edge of the side pot wall to inhibit excessive exposure of the roots passing through the slit area 11 to the air and inhibit blocking of a laser beam running through the slit area 11 by too much substrate.

To sum up, the bottom pot 12 and the insert pot 13, and the two adjacent insert pots 13 are connected and fixed by means of three pins and pin holes that are made of a high-strength material, respectively, thereby ensuring that one slit area 11 is formed between the bottom pot 12 and the adjacent insert pot 13, and the other slit area 11 is formed between the two adjacent insert pots 13.

In this example, the two laser measuring units 20 are exactly the same in structure and function, which are arranged in such a manner of corresponding to the two slit areas 11 one to one. Here, only one of the laser measuring units 20 is described in detail, while the detailed description of the other is omitted.

Figure 3:
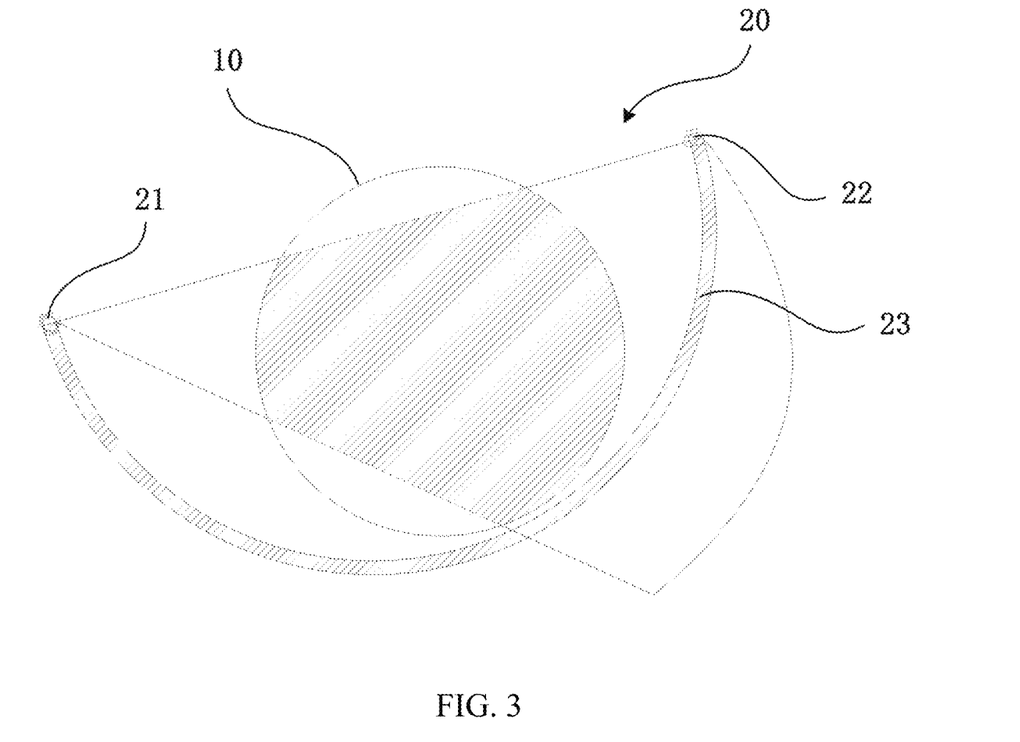
FIG. 3 is a schematic diagram of measurement of a laser measuring unit according to an example of the disclosure.

FIG. 3 is a schematic diagram of measurement of a laser measuring unit according to an example of the disclosure.

As shown in FIG. 1 and FIG. 3, the laser measuring unit 20 has a laser transmitter 21, a receiver 22 and an arc-shaped measuring bow 23 disposed corresponding to the slit area 11.

The laser transmitter 21 and the receiver 22 are fixed to the two ends of the arc-shaped measuring bow 23, respectively, in such a manner that the laser transmitter 21 and the receiver 22 are located on opposite sides of the plant pot 10. Thus, it can be ensured that a laser beam emitted by the laser transmitter 21 face the receiver 22 directly, and it can also be ensured that the beam path is horizontal and extends through the cross section of the slit area 11 of the plant pot 10.

In this example, the arc-shaped measuring bow 23 is mounted on a column fixed to the base of the rotating stage 30 and then actuated to rotate around the laser transmitter 21 as the starting point of a beam back and forth at a uniform speed by an angle $\alpha$. Whether a beam path is blocked is detected at a fixed time interval, so that detection results of m beam paths distributed at equal angles are obtained. Each time the arc-shaped measuring bow completes a swing, a detection sector is defined between the starting detection beam path and the end detection beam path. An overlapping area between the sector and the cylindrical cross section of the plant pot 10 is an effective detection area of a swing (as shown in the shadow in FIG. 3). The arc-shaped measuring bow 23 can be optimally designed so that it can swing by the angle $\alpha$ about the center line of the diameter of the plant pot 10 while the shortest distance between the laser transmitter 21 and the receiver 22 is maintained, thereby being conducive to improving the detection sensitivity.

In this example, the laser beam emitted by the laser transmitter 21 has a diameter of less than 1 mm.

As shown in FIG. 1, the plant pot 10 with the plant to be measured is placed on the rotating stage 30 in such a manner that the centers of the two are vertically and coaxial with each other.

In this example, a high-precision equal-angle stepping motor is used to drive the rotating stage 30, so that the plant pot 10 rotates step by step around a central axis. A swing detection of the arc-shaped measuring bow 23 is completed at each interval between steps. The stepping motor is set to rotate each time by an angle $\beta$, and then there are n intervals between steps (n=360/$\beta$) after the motor rotates a circle. The passing or blocking signals of m×n beam paths are detected over the entire cycle.

The data analyzing unit is in communication connection with the two laser measuring units 20 and configured to statistically analyze the roots of the plant to be measured based on the laser measuring results and finally realize accurate measurement on all the roots in the slit area 11. In this example, the function of the data analyzing unit is implemented on a computer. Here, the laser measuring result refers to a beam path passing signal or a beam path blocking signal obtained by a laser beam emitted from the laser transmitter 21 to the corresponding receiver 22. Specifically, when a laser beam is blocked by roots, the measuring result of the current beam is the beam path blocking signal; and when a laser beam is not blocked by roots, the measuring result of the current beam is the beam path passing signal.

Figure 4:
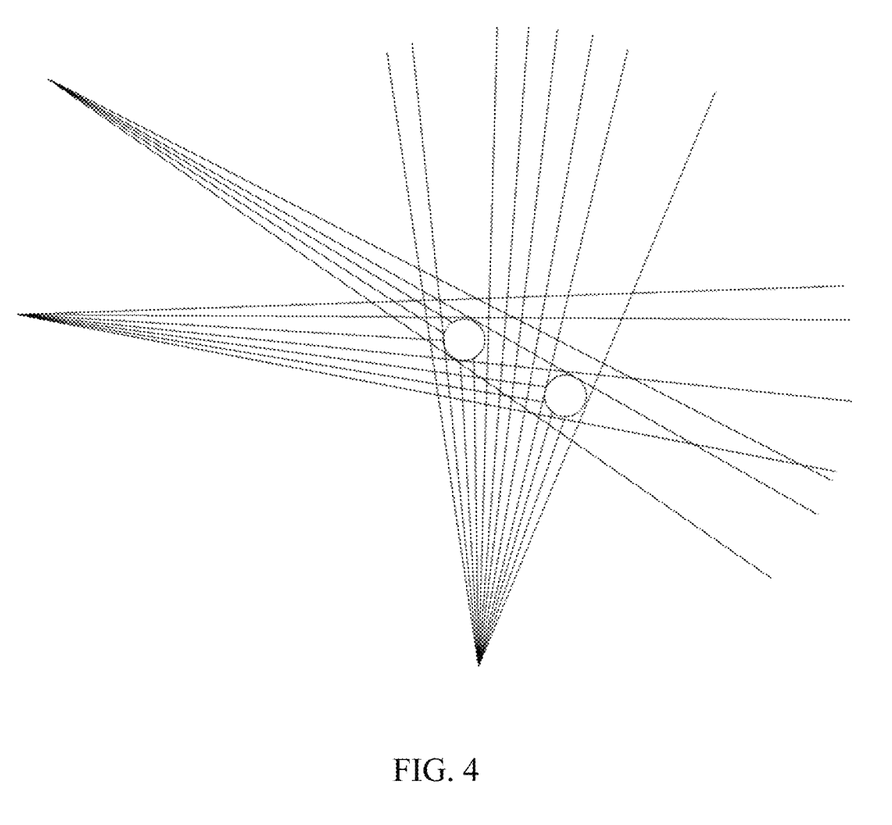
FIG. 4 is a schematic diagram of passing and blocking of paths of laser beams according to an example of the disclosure.

FIG. 4 is a schematic diagram of passing and blocking of paths of laser beams according to an example of the disclosure.

As shown in FIG. 4, laser measurement is performed at three angles in one slit area 11, and three detection sectors are created. The coordinate positions of all detection beam paths in the three detection sectors within the slit area are analyzed and reconstructed by the data analyzing unit, and then fault localization and counting of roots in the cross section can be performed according to the coverage of the laser path passing and blocking signals in the cross section and the intersection position information of the blocked beam paths.

Specifically, cross-sectional boundaries of roots can be effectively defined by the passing and blocking information of the laser beam paths around two predetermined root system cross sections. By overlapping the cross section of the plant pot 10 with n detection sectors or effective detection areas, a sufficient number of detection beams at various angles can "illuminate" all the gaps between the roots. Even if there are a large number of roots in the cross section that block each other, fault localization and counting can be performed on most of the roots.

Root angles and the ratio of deep roots to shallow roots can be further estimated based on the detection on the number and distribution of roots in a cross section at a specific depth in this example. The specific solution is as follows:

When a root system architecture is detected according to this example, the base of the plant to be measured is positioned at the center of the substrate surface of the plant pot 10 that is regarded as the root system attachment position (point a). A slit area 11 is pre-formed at a specified depth (h) below the soil surface. Assuming that a distance between the cross-sectional central point (point b) of a particular root localized in a detection fault in the slit area 11 and the central point of the detection fault is x, an included angle between the line connecting points a and b and the horizontal plane is $\gamma=\arctan(x/h)$. By this method, the growth angle of each root can be estimated, so that phenotyping indicators such as an average growth angle, a variation extent and frequency distribution for the roots of the plant to be measured can be obtained.

In view of critical angles to distinguish between deep roots and shallow roots that has been determined in existing research methods, for example, in rice, those growing at an angle of less than 50 degrees with respect to the horizontal are considered as shallow roots, while those growing at an angle of greater than 50 degrees with respect to the horizontal are considered as deep roots. Thus, shallow roots and deep roots can be distinguished by comparing the above estimated growth angles of the roots with the specified critical value, and respective numbers of such roots are counted. Thus, the phenotyping indicator, a ratio of deep roots, can be calculated.

In the cross section of the slit area 11, a circle centered in the central point and having the radius $r=h\times\tan(\gamma)$ can be defined according to a height (h) between the detection fault to the substrate surface and an agreed critical angle for deep and shallow roots ($\gamma$) in the plant to be measured, the roots localized within the circle are deep roots, while those localized outside the circle are shallow roots. The respective numbers of the deep roots and the shallow roots are counted, and then the phenotyping indicator, the ratio of deep roots, can also be calculated.

Figure 5:
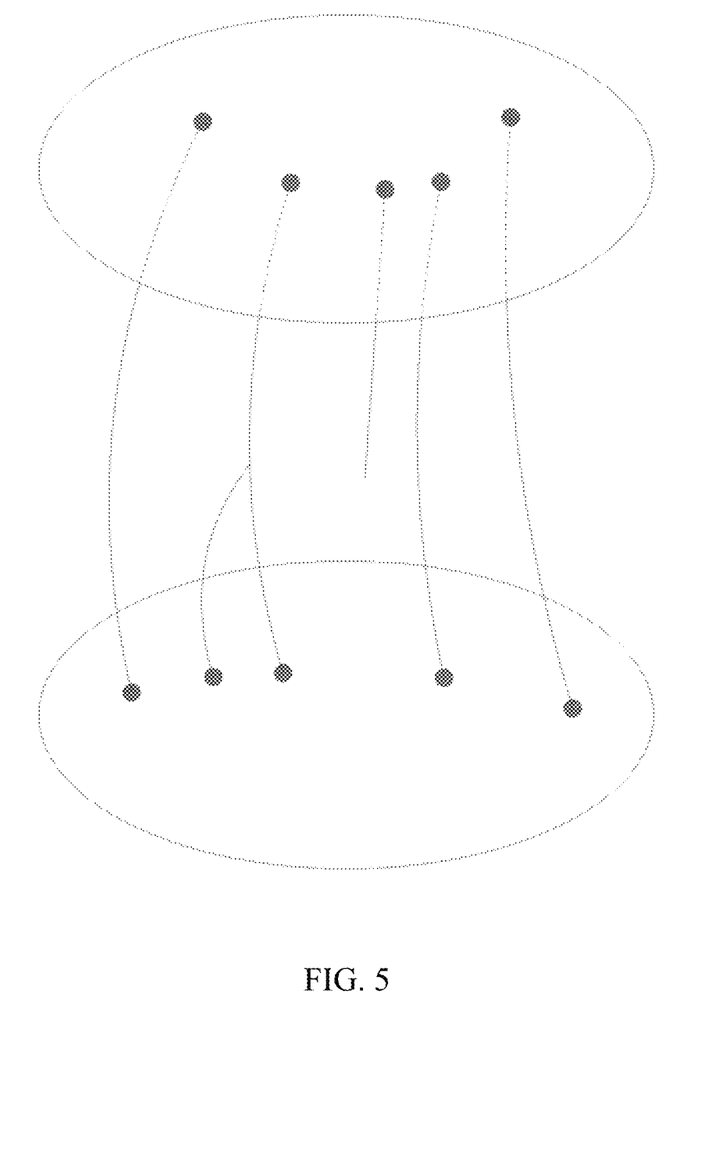
FIG. 5 is a schematic diagram of a pseudo-three-dimensional root system architecture according to an example of the disclosure.

FIG. 5 is a schematic diagram of a pseudo-three-dimensional root system architecture according to an example of the disclosure.

As shown in FIG. 1 and FIG. 5, after the plant roots are measured and localized in two slit areas 11, respectively, the above fault localization and counting techniques for roots are subjected to verification and parameter optimization. A relationship between the increase in the number of roots and a detection error is estimated, and a regression model between the actual number of roots and a count obtained by detection is established. Finally, the regression equation between the number of roots detected by this technique and the actual number of roots is verified and applied based on the actual measuring results of roots of a plurality of genotypes of the plant to be measured in different periods. Moreover, integrated analysis is performed on the detection data of the positions and numbers of roots in the cross sections of the two slit areas 11, and then a pseudo-three-dimensional root system architecture of the plant to be measured as shown in FIG. 5 can be reconstructed. The specific solution is as follows:

The roots of the plant to be measured have the features of growing towards the center of the earth and diverging from the center. According to a vertical projection relationship between root localization coordinates in the fault of an upper slit area and root localization coordinates in the fault of a lower slit area, two root cross sections that completely coincide with or are closer to each other in position are connected by a straight line or a smooth curve, regarded as a root. In similar ranges, if only one root is localized in the upper fault while two roots are localized in the lower fault, two localization points having closer projection positions up and down are connected, regarded as a main root or a higher-order lateral root, and the middle position of the main root or the lateral root is connected to the remaining localization point in the lower fault by a smooth curve, regarded as a lateral root of the main root or a lateral root inferior to a lateral root of a particular order. In similar ranges, if two roots are localized in the upper fault and only one root localized in the lower fault, it is regarded that the root tip of one of the roots is localized at ½ height vertically down from the localization position in the upper fault. Similarly, a main root-lateral root relationship, a root tip position, a root trend curve and the like are optimized according to an existing database and more fault localization information of the root system architecture of the plant to be measured, and a pseudo-three-dimensional root system architecture is then constructed.

Purposes and Effects of the Example

According to the system for detection and analysis of a fibrous root system architecture of a plant in this example, a horizontal slit area is pre-formed in the plant pot, and a sector transmission detection field of view is created by the laser transmitter swinging horizontally. Full coverage of detection beam lights at multiple angles in the cross section is affected by constant-speed rotation of the rotating stage and the arc-shaped measuring bow relative to each other. Beam path passing and blocking signals are reconstructed and analyzed by the data analyzing unit to identify the distribution of roots in the cross section, and the number of the roots is counted. Furthermore, a pseudo-three-dimensional root system architecture is reconstructed according to the fault analysis results of a plurality of slit areas up and down.

In a variant, the vertical position of the arc-shaped measuring bow on the base column of the rotating stage is continuously adjustable, and can be locked after the adjustment is completed to keep a beam path of the laser transmitter in a horizontal position. A plurality of arc-shaped measuring bows can be installed on one rotating stage, and the heights of the bows are respectively adjusted to the corresponding pre-formed slit areas, allowing for simultaneous laser transmission detection on two or more slit areas up and down. As a result, the detection efficiency can be improved, and the required detection time for a multi-slit plant pot can be shortened.

In a variant, a multi-path detection sector can be formed between one laser transmitter and a plurality of receivers distributed in an arc. Alternatively, a directional beam rotates at a constant speed to irradiate the plurality of receivers distributed in an arc in sequence, thereby achieving multi-path sector transmission detection. As a result, the arc-shaped measuring bow can be omitted, so that the system can be simplified and the detection efficiency can be improved.

In a variant, laser photoelectric sensors with different wavelengths or a plurality of pairs of anti-interference photoelectric sensors are installed at the corresponding positions in the same slit area to form a plurality of cross detection beam paths. In this way, the detection efficiency can be also improved.

Compared with the prior art, the technical solution provided by the disclosure has the following beneficial effects:

1) The growth situation and spatial distribution of the roots of the plant to be measured in the plant pot of the disclosure are closer to the root system architecture in the field soil as compared with plant roots in the transparent media, or in compressed two-dimensional space, or under hydroponic conditions.

2) According to the disclosure, fault transmission detection is performed on the roots through the slit areas, which can be regarded as a non-invasive observation method. The root system architecture can be detected for a plurality of times during the growth of the plant, thereby obtaining the continuous monitoring results of the dynamic changes of the root system architecture.

3) According to the disclosure, the transmission detection using visible light beams, compared with CT or MM detection techniques for plant roots, has the advantages of low cost, no risk of ionizing radiation, and greatly improved resolution at the same investment level.

4) The soil mass is divided into a plurality of soil layers up and down by the pre-formed slit areas. If necessary, different volumes of irrigation water and different nutrient contents can be applied to different soil layers, for example, to simulate the differences in moisture and nutrient availability between deep and shallow layers of soil in the field.

Although the specific examples of the disclosure have been described above, those skilled in the art will understand that the foregoing description is illustrative only, and the protection scope of the disclosure is defined by the appended claims. Those skilled in the art can make various changes or modifications to such examples without departing from the principle and essence of the disclosure, but these changes and modifications shall fall within the protection scope of the disclosure.

What is claimed is:

1. A system for detection and analysis of a fibrous root system architecture of a plant, comprising:
    a plant pot for growing a plant to be measured, the plant pot having at least one slit area extending through a cross section in an axial direction;
    at least one laser measuring unit, each laser measuring unit having a laser transmitter and a receiver disposed corresponding to the slit area in such a manner that a laser beam emitted from the laser transmitter to the receiver goes across the cross section of the plant pot;
    an arc-shaped measuring bow for mounting the laser measuring unit and driving the laser measuring unit to swing horizontally around the laser transmitter within a predetermined angle range to realize measurement of roots in an effective sector;
    a rotating stage for driving the plant pot to rotate step by step by an equal angle to obtain measuring results of roots in a plurality of effective sectors sequentially at different angles, thus realizing measurement of roots exposed in the slit area; and
    a data analyzing unit connected to the laser measuring unit to statistically analyze the roots of the plant to be measured based on laser measuring results.

2. The system for detection and analysis of a fibrous root system architecture of a plant according to claim 1, wherein
    the plant pot comprises a bottom pot and at least one insert pot capable of being inserted into the bottom pot;
    the slit area is formed between the bottom pot and the adjacent insert pot; and
    the bottom of the insert pot is of a mesh structure having a mesh aperture greater than a maximum root diameter of the plant to be measured.

3. The system for detection and analysis of a fibrous root system architecture of a plant according to claim 2, wherein
    at least two insert pots are used with the slit area being formed between every two adjacent insert pots;
    the number of the laser measuring units is the same as that of the insert pots; and
    each slit area is provided with the laser transmitter and the receiver.

4. The system for detection and analysis of a fibrous root system architecture of a plant according to claim 3, wherein
    the bottom pot and the insert port or every two adjacent insert pots are connected and fixed by means of a plurality of pins and corresponding pin holes.

5. The system for detection and analysis of a fibrous root system architecture of a plant according to claim 4, wherein
    an end, corresponding to the laser transmitter, of the arc-shaped measuring bow is fixed to a column that is mounted on a fixed base of the rotating stage.

6. The system for detection and analysis of a fibrous root system architecture of a plant according to claim 5, wherein
    a laser beam emitted by the laser transmitter has a diameter of less than 1 mm, and
    the laser measuring result is a beam path passing signal or a beam path blocking signal obtained by a laser beam emitted by the laser transmitter to the corresponding receiver.

7. The system for detection and analysis of a fibrous root system architecture of a plant according to claim 6, wherein
    during the rotation of the arc-shaped measuring bow, the laser measuring unit performs detection for a plurality of times at a predetermined time interval, thereby defining a detection sector.

8. The system for detection and analysis of a fibrous root system architecture of a plant according to claim 7, wherein
    the plant pot is placed on the rotating stage in such a manner that centers of the pots are vertically coaxial with each other; and during the process that the plant pot rotates a circle step by step by an equal angle, the laser measuring unit swings once at each interval between steps to measure roots, thereby obtaining measuring results of roots for a plurality of detection sectors.

9. The system for detection and analysis of a fibrous root system architecture of a plant according to claim 8, wherein the data analyzing unit reconstructs the coordinate positions of all detection beam paths in the slit area by analysis, and performs fault localization and counting of roots in the cross section according to the coverage of the laser beams in the cross section and the intersection position information of blocked beam paths.

10. The system for detection and analysis of a fibrous root system architecture of a plant according to claim 9, wherein the data analyzing unit also performs integrated analysis on the detection data of the positions and numbers of roots in the cross sections of a plurality of slit areas so as to realize the reconstruction of a pseudo-three-dimensional root system architecture of the plant to be measured.

* * * * *